United States Patent [19]

Spector

[11] Patent Number: 4,544,592
[45] Date of Patent: Oct. 1, 1985

[54] AROMA-GENERATING CAPSULE

[76] Inventor: Donald Spector, 380 Mountain Rd., Union City, N.J. 07087

[21] Appl. No.: 656,768

[22] Filed: Oct. 1, 1984

[51] Int. Cl.⁴ .......................... B32B 3/16; A61L 9/02
[52] U.S. Cl. ...................................... 428/68; 428/905; 239/56
[58] Field of Search .................... 428/68, 74, 905; 239/53, 55, 56, 57, 34

[56] References Cited

U.S. PATENT DOCUMENTS

| | | | |
|---|---|---|---|
| 877,309 | 1/1908 | Emerson | 239/55 |
| 1,920,599 | 9/1933 | Schuh | 422/125 |
| 2,372,371 | 3/1945 | Eisner | 239/34 |
| 2,435,756 | 2/1948 | Schlesinger | 239/34 |
| 2,591,818 | 4/1952 | Huff | 422/125 |
| 2,615,754 | 10/1952 | Lindenberg | 239/56 |
| 4,277,024 | 7/1981 | Spector | 239/36 |
| 4,283,011 | 9/1981 | Spector | 239/36 |
| 4,346,059 | 10/1982 | Spector | 428/905 |
| 4,493,011 | 1/1985 | Spector | 428/905 |

*Primary Examiner*—John E. Kittle
*Assistant Examiner*—Thomas C. Saitta
*Attorney, Agent, or Firm*—Michael Ebert

[57] ABSTRACT

An aroma-generating miniature capsule adhesively attachable to the surface of an incandescent light bulb to be activated by heat emanating therefrom. The capsule, preferably formed of a flexible synthetic plastic skin, includes a top wall having a vent hole therein and a base wall provided with a pressure-sensitive outer coating to adhere the capsule to the bulb. Supported within the internal cavity of the capsule is a pad of porous material having good wicking properties impregnated with a volatile aromatic liquid. The pad is at a position within the cavity adjacent the top wall to define therebelow an air chamber which when heated creates a positive air pressure forcing a stream of heated air through the pad to produce a vaporous scent. This is discharged into the atmosphere through the vent hole.

7 Claims, 5 Drawing Figures

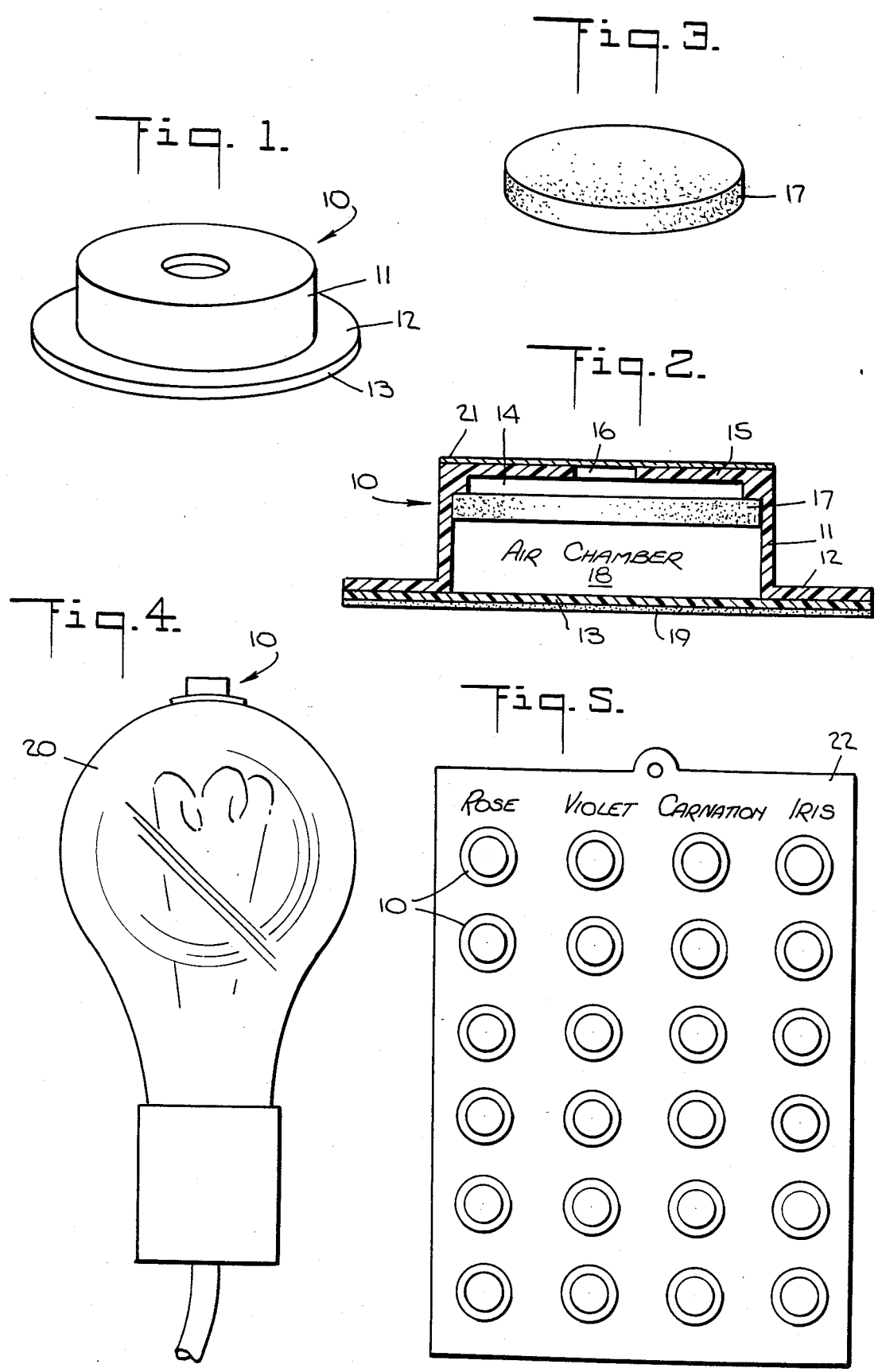

AROMA-GENERATING CAPSULE

BACKGROUND OF INVENTION

1. Field of Invention

This invention relates generally to aroma-generating devices for wafting into the atmosphere a pleasant scent or other aroma, and more particularly to an aroma-generating miniature capsule which is adhesively attachable to the surface of an incandescent light bulb to be activated by heat emanating from the bulb.

2. Prior Art

As used herein, the term "aroma" is not limited to pleasant or savory smells, but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oils of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

An incandescent light bulb is an inefficient converter of electrical to light energy, for a substantial portion of the electrical energy is transformed into non-visible heat. It is for this reason that light bulbs are sometimes used as heat sources in vaporizers for suffusing a vapor into the atmosphere surrounding the bulb having medicinal, disinfecting or perfuming qualities.

Thus the Schuh U.S. Pat. No. 1,920,599 discloses a slotted disc formed of porous filter paper impregnated with a volatile solution, the disc fitting onto a light bulb. Heat radiated from the bulb brings about rapid vaporization of the impregnant. When the disc is exhausted, it may be removed from the bulb and discarded.

In the Huff U.S. Pat. No. 2,591,818, a light bulb is mounted at the base of a chimney to produce an upwardly-flowing stream of heated air which passes through a wicking element impregnated with a vaporizable liquid. In the Cartwright U.S. Pat. No. 2,501,496, a heated air stream produced by a light bulb is directed over a dish containing a volatile liquid.

In the Eisner U.S. Pat. No. 2,372,371, a porous pad saturated with a deodorant is held in a small container mounted directly on an electric light bulb. Similar bulb arrangements to promote vaporization re disclosed in the Guderman U.S. Pat. No. 1,403,548, and in the Schlesinger U.S. Pat. No. 2,437,756.

All of these prior art bulb-activated aroma generators are more or less complex and relatively expensive.

SUMMARY OF INVENTION

In view of the foregoing, the main object of this invention is to provide an aroma-generating miniature capsule which is adhesively attachable directly onto the contoured surface of an electric light bulb, the capsule being activated by heat emanating from the bulb to discharge a vaporous scent into the atmosphere surrounding the bulb.

A significant advantage of the invention is that the user is able to quickly attach an aroma-generating capsule to the bulb, and to just as quickly remove the capsule from the bulb when it is exhausted.

Because the capsules are in miniature form, they do not interfere with the light radiated from the bulb. Also, more than one capsule may be attached to the bulb, the attached capsules generating different scents to create a desired blend thereof.

Also an object of the invention is to provide a miniature aroma-generating capsule which, despite its small size and low cost, is a highly efficient aroma generator, in that it includes an impregnated porous pad that is subjected to a pressurized stream of heated air.

Briefly stated, these objects are attained in an aroma-generating miniature capsule adhesively attachable to the surface of an incandescent light bulb to be activated by heat emanating therefrom. The capsule, preferably formed of a flexible synthetic plastic skin, includes a top wall having a vent hole therein and a base wall provided with a pressure-sensitive outer coating to adhere the capsule to the bulb. Supported within the internal cavity of the capsule is a pad of porous material having good wicking properties impregnated with a volatile aromatic liquid. The pad is at a position within the cavity adjacent the top wall to define therebelow an air chamber which when heated creates a positive air pressure forcing a stream of heated air through the pad to produce a vaporous scent. This is discharged into the atmosphere through the vent hole.

OUTLINE OF DRAWING

For a better understanding of the invention as well as other objects and further features thereof, reference is made to the following detailed description to be read in conjunction with the accompanying drawings, wherein:

FIG. 1 is a perspective view of an aroma-generating capsule in accordance with the invention;

FIG. 2 is a section taken through the capsule;

FIG. 3 is a separate perspective view of the porous pad included in the capsule;

FIG. 4 illustrates an electric light bulb having a capsule adhesively attached thereto; and FIG. 5 is a display card having an array of removable capsules mounted thereon.

DESCRIPTION OF INVENTION

Referring now to FIGS. 1, 2 and 3, there is shown a miniature capsule in accordance with the invention, generally designated by numeral 10, constituted by a hat-shaped cylindrical upper section 11 having an annular brim 12 to which is bonded a base disc 13 to define an internal cavity 14. The top wall 15 is provided at its center with a vent hole 16.

The upper section 11 and base disc 13 are preferably formed of a flexible, synthetic plastic skin or of film material such as "Mylar" polyester, polyethylene, or PVC capable of withstanding the heat generated by the electric light bulb to which the capsule is adhesively attached. Alternatively, the capsule skin may be formed of a metal-foil plastic film laminate.

Brim 12 of the upper section may be joined to the base disc 12 by a heat-resistant bonding agent such as an epoxy, or by ultrasonic sealing so that the internal cavity 14 is hermetically sealed, but for vent hole 16.

Mounted within the internal cavity 14 of the capsule at a position adjacent the upper wall 15 is a disc-shaped pad 17 formed of porous material having good wicking properties, such as blotting paper, open-cell foam plastic material or non-woven fabric. The pad is parallel to the base disc 13 to define therebetween a confined air chamber 18.

Pad 17 is impregnated, preferably through vent hole 16, with a volatile liquid fragrance which is wicked throughout the entire body of the pad so that the pad is fully saturated. The liquid fragrance may have a fruit scent, a flower scent, or any other natural or synthetic fragrance. Thus, one may provide aroma-generating capsules in a great variety of fragrances, permitting the user to select whichever fragrance is appropriate gor a given occasion. The invention is not limited to pleasing scents, and capsules may be impregnated to function as deodorizers, as insect repellents or as disinfectants.

The undersurface of the base disc 13 is coated with a low-tack pressure-sensitive adhesive layer 19 which is heat resistant. For this purpose, an elastomeric mass coat may be used that will afford a bond of moderate strength upon application of only light pressure.

When capsule 10 is adhesively attached to the contoured surface of a light bulb 20, as shown in FIG. 4, because its skin is flexible, the base 13 of the capsule will conform to the surface of the bulb regardless of where it is placed. When the capsule is exhausted, it may be peeled off the lamp and discarded.

When bulb 20 is turned on, the heat generated thereby acts to heat the air in the confined air chamber 18 in the attached capsule. As a consequence, the air expands and the resultant positive pressure forces the heated air through the porous pad 17 to volatilize the liquid fragrance impregnated therein. The vaporous scent is discharged into the atmosphere surrounding the bulb through vent hole 16.

In practice, the capsule may be provided with a removable sticker 21, shown only in FIG. 2, to seal vent hole 16 and thereby prevent the loss of scent when the capsule is being stored, so that the capsule has a prolonged storage life. Base 13 may be provided with a peel-off sheet (not shown) to protect the sticky adhesive layer.

Instead of using a peel-off protective sheet, an array of capsules 10 may be mounted on a display board 22, as shown in FIG. 5, having a smooth coated face surface onto which the capsules are adhesively attached. The nature of the coated face is such that the capsules may be readily released therefrom.

The display card is printed to identify the scent (Rose, Violet, Carnation, Iris) in each row of capsules mounted thereon so that the user can choose whiever scent he wishes to generate in conjunction with the lamp. And because the user has a choice of scents, he can apply more than one capsule to the bulb and thereby generate a blend of different scents. Though flower scents are shown, in practice, the user may be given a choice of fruit or other distinctive scents. Instead of a display card, the capsules may be made in strip form, with a perforation between adjacent capsules, so that they may be separated from the strip.

While there has been shown and described a preferred embodiment of an aroma-generating capsule in accordance with the invention, it will be appreciated that many changes and modifications may be made therein without, however, departing from the essential spirit thereof. Thus, instead of placing the porous pad within the cavity at a position therein creating a distinct air chamber below the pad, the pad may be dimensioned to occupy almost the entire cavity within the plastic envelope so that the air entrapped in the interstices of the fibers forming the pad acts effectively as the air chamber to produce a positive pressure when the air is heated.

1. An aroma generating miniature capsule attachable to the contoured surface of an incandescent light bulb to be activated by heat emanating therefrom, the capsule comprising:
   A. an envelope of flexible skin material defining an internal cavity bounded by a top wall having a vent hole therein and a base wall having a heat-resistant pressure-sensitive outer coating thereon, whereby the capsule may be adhesively attached to the bulb surface to conform thereto; and
   B. a pad of porous material impregnated with a volatile aromatic liquid supported within the cavity at a position adjacent the top wall to define an entrapped air pocket therebelow, whereby when the air in the pocket is heated and expanded by the heat emanating from the bulb, the resultant positive pressure forces the heated air through the pad to volatilize the liquid to produce an aromatic vapor which is discharged into the atmosphere through the vent hole.

2. A capsule as set forth in claim 1, wherein said skin is formed of synthetic plastic material.

3. A capsule as set forth in claim 1, wherein said skin is of polyester.

4. A capsule as set forth in claim 1, wherein said pad is of blotting paper.

5. A capsule as set forth in claim 1, wherein said volatile liquid is a perfume.

6. A capsule as set forth in claim 1, further including a peel-off cover on said top wall to seal the vent hole.

7. A capsule as set forth in claim 1, wherein said envelope is formed of a top section having a hat formation provided with an annular brim which is bonded to a disc-shaped base wall.

* * * * *